(12) United States Patent
Edenhoffer

(10) Patent No.: US 11,413,408 B2
(45) Date of Patent: Aug. 16, 2022

(54) POSITIVE PRESSURE INSPIRATION DEVICE FOR DELIVERY OF MEDICAMENTS

(71) Applicant: Peter Edenhoffer, Paris, TX (US)

(72) Inventor: Peter Edenhoffer, Paris, TX (US)

(*) Notice: Subject to any disclaimer, the term of this patent is extended or adjusted under 35 U.S.C. 154(b) by 235 days.

(21) Appl. No.: 16/914,002

(22) Filed: Jun. 26, 2020

(65) Prior Publication Data
US 2020/0324062 A1 Oct. 15, 2020

Related U.S. Application Data

(63) Continuation-in-part of application No. 14/812,887, filed on Jul. 29, 2015, now abandoned.
(Continued)

(51) Int. Cl.
| | |
|---|---|
| *A61M 11/02* | (2006.01) |
| *A61M 16/20* | (2006.01) |
| *A61M 16/10* | (2006.01) |
| *A61M 16/00* | (2006.01) |
| *A61M 16/06* | (2006.01) |

(Continued)

(52) U.S. Cl.
CPC ........... *A61M 11/02* (2013.01); *A61M 11/005* (2013.01); *A61M 11/06* (2013.01); *A61M 16/0006* (2014.02); *A61M 16/0063* (2014.02); *A61M 16/0683* (2013.01); *A61M 16/0875* (2013.01); *A61M 16/1065* (2014.02); *A61M 16/208* (2013.01); *A61M 2016/0024* (2013.01); *A61M 2016/0027* (2013.01); *A61M 2202/0427* (2013.01); *A61M 2202/0437* (2013.01); *A61M 2202/07* (2013.01); *A61M 2205/3331* (2013.01); *A61M 2205/50* (2013.01)

(58) Field of Classification Search
None
See application file for complete search history.

(56) References Cited

U.S. PATENT DOCUMENTS

| | | |
|---|---|---|
| 2,693,178 A | 11/1954 | Gilroy |
| 3,045,668 A | 7/1962 | Lee |

(Continued)

FOREIGN PATENT DOCUMENTS

| | | |
|---|---|---|
| DE | 19939417 A1 | 3/2001 |
| DE | 102008050218 A1 | 7/2009 |

(Continued)

OTHER PUBLICATIONS

English Translation of "DE 19939417 A1", https://worldwide.espacenet.com, Oct. 31, 2018.
(Continued)

*Primary Examiner* — Margaret M Luarca
*Assistant Examiner* — Cana A Gallegos
(74) *Attorney, Agent, or Firm* — Workman Nydegger

(57) ABSTRACT

A respiratory system includes a nebulizer pneumatically connected to a breathing unit. A pressure sensitive mechanism detects negative pressure at the breathing unit due to inspiration and initiates nebulization. The nebulizer is configured to cease nebulization prior to the end of inspiration. Residual medicament disposed in the system is cleared from the system and delivered to the patient during the remainder of the inspiration cycle. A compressor provides positive pressure to aid delivery of medicaments to the patient.

19 Claims, 4 Drawing Sheets

Related U.S. Application Data

(60) Provisional application No. 62/030,223, filed on Jul. 29, 2014.

(51) Int. Cl.
  *A61M 16/08* (2006.01)
  *A61M 11/00* (2006.01)
  *A61M 11/06* (2006.01)

(56) References Cited

U.S. PATENT DOCUMENTS

| | | | |
|---|---|---|---|
| 3,434,471 | A | 3/1969 | Liston |
| 3,976,064 | A | 8/1976 | Wood et al. |
| 4,076,021 | A | 2/1978 | Thompson |
| 4,319,155 | A | 3/1982 | Nakai et al. |
| 4,558,710 | A | 12/1985 | Eichler |
| 4,905,683 | A | 3/1990 | Cronjaeger |
| 5,054,477 | A | 10/1991 | Terada et al. |
| 5,322,057 | A | 6/1994 | Raabe et al. |
| 5,479,920 | A | 1/1996 | Piper et al. |
| 5,511,538 | A | 4/1996 | Haber et al. |
| 5,570,682 | A | 11/1996 | Johnson |
| 5,584,285 | A | 12/1996 | Salter et al. |
| 5,592,935 | A | 1/1997 | Elstran et al. |
| 5,813,401 | A | 9/1998 | Radcliff et al. |
| 5,823,179 | A | 10/1998 | Grychowski et al. |
| 5,826,570 | A | 10/1998 | Goodman et al. |
| 5,850,835 | A | 12/1998 | Takaki et al. |
| 6,105,929 | A | 8/2000 | Davenport et al. |
| 6,412,481 | B1 | 7/2002 | Bienvenu et al. |
| 6,557,549 | B2 | 5/2003 | Schmidt et al. |
| 6,772,754 | B1 | 8/2004 | Mendenhall |
| 7,073,769 | B2 | 7/2006 | Bauer et al. |
| 7,841,335 | B2 | 11/2010 | Harrington et al. |
| 8,113,194 | B2 | 2/2012 | Boehm et al. |
| 8,342,171 | B2 | 1/2013 | Boehm et al. |
| 8,671,934 | B2 | 3/2014 | Addington et al. |
| 8,746,247 | B2 | 6/2014 | Mechlenburg |
| 9,744,314 | B2 | 8/2017 | Keller et al. |
| 9,757,528 | B2 | 9/2017 | Rubin |
| 2002/0157663 | A1 | 10/2002 | Blacker et al. |
| 2003/0196660 | A1 | 10/2003 | Haveri |
| 2004/0134494 | A1 | 7/2004 | Papania et al. |
| 2004/0173209 | A1 | 9/2004 | Grychowski et al. |
| 2004/0200476 | A1 | 10/2004 | Bamford |
| 2005/0229929 | A1 | 10/2005 | Ivri |
| 2005/0235993 | A1 | 10/2005 | Baecke et al. |
| 2005/0263150 | A1 | 12/2005 | Chathampally et al. |
| 2005/0284469 | A1 | 12/2005 | Tobia et al. |
| 2006/0162722 | A1 | 7/2006 | Boehm et al. |
| 2006/0191537 | A1 | 8/2006 | Muellinger et al. |
| 2006/0243277 | A1* | 11/2006 | Denyer ............ A61M 15/0085 128/200.14 |
| 2007/0131230 | A1 | 6/2007 | Giroux |
| 2007/0157931 | A1 | 7/2007 | Parker et al. |
| 2007/0227535 | A1 | 10/2007 | Harrington et al. |
| 2007/0227536 | A1 | 10/2007 | Rivera et al. |
| 2008/0047559 | A1 | 2/2008 | Fiori |
| 2008/0066741 | A1 | 3/2008 | Lemahieu et al. |
| 2008/0257348 | A1 | 10/2008 | Piper |
| 2010/0319687 | A1 | 12/2010 | Esaki et al. |
| 2013/0164338 | A1 | 6/2013 | Lipp et al. |
| 2013/0180524 | A1 | 7/2013 | Shahaf et al. |
| 2013/0327323 | A1 | 12/2013 | Rubin |
| 2014/0290646 | A1* | 10/2014 | Koehler ............ A61M 15/009 128/203.14 |
| 2014/0301871 | A1 | 10/2014 | Rogers, Jr. |
| 2016/0193438 | A1 | 7/2016 | White et al. |

FOREIGN PATENT DOCUMENTS

| | | |
|---|---|---|
| EP | 0519742 A1 | 12/1992 |
| EP | 1857133 A1 | 11/2007 |
| EP | 2119465 A1 | 11/2009 |
| EP | 2537548 A2 | 12/2012 |
| FR | 2799978 A1 | 4/2001 |
| JP | 2005-536307 A | 12/2005 |
| WO | 01/32267 A1 | 5/2001 |
| WO | 2004/020029 A1 | 3/2004 |
| WO | 2007/064657 A1 | 6/2007 |
| WO | 2009/035901 A1 | 3/2009 |
| WO | 2009/042187 A1 | 4/2009 |

OTHER PUBLICATIONS

English Translation of "FR 2799978 A1", https://worldwide.espacenet.com, Oct. 31, 2018.

Extended European Search Report cited in EP15827303.7 dated Mar. 6, 2018.

ISR cited in PCT Application No. PCT/US2015/042738 dated Nov. 13, 2015.

* cited by examiner

POSITIVE PRESSURE INSPIRATION DEVICE FOR DELIVERY OF MEDICAMENTS

CROSS-REFERENCE TO RELATED APPLICATION

This application is a continuation-in-part of U.S. application Ser. No. 14/812,887, filed Jul. 29, 2015, which claims the benefit of U.S. Provisional Patent Application No. 62/030,223, filed Jul. 29, 2014, each of which are incorporated herein in their entirety.

BACKGROUND

Degenerative processes which occur as a result of normal aging or disease processes can affect all humans and animals. The treatment of pathological and normal degenerative processes affecting different organs faces various obstacles such as accessing the organs and finding effective treatments.

Most organ systems can be accessed via the arterial and venous circulatory system. A less common route is via the nasopharyngeal and pulmonary system. Medications administered through the nasopharyngeal and pulmonary system may reach the nasal cavities, pharynx, larynx, trachea, bronchi, alveoli, and associated vascular and connective tissue structures.

In addition, in most animals, the nasal cavities provide a potential portal to the central nervous system (CNS) through the olfactory nerves and associated vascular and connective tissue structures surrounding the olfactory bulb.

Currently, inhaled medications are administered into the nasopharyngeal passageways with simple sprays, inhalers, and nebulizers. These methods result in only partial absorption of the introduced materials into the body. Additionally, patients with significant pulmonary disease may have to exert great effort during the respiratory treatment, rendering the patient physically unable to complete the inhalation treatment.

Further, devices for administering medicaments to the nasopharyngeal passageways are typically configured to provide medicaments at a constant rate, resulting in waste of the medicaments. For example, nebulizers are typically configured to continuously channel and/or nebulize a source of medicament to a patient to be delivered to target treatment areas as the patient inspires. In such devices, however, a significant amount of the medicament is wasted. In particular, medicament is wasted during patient expiration, when medicament cannot be delivered to the patient, but is instead undesirably passed out of the device, passed into other areas of the device (becoming trapped in filters and/or potentially contaminating the medicament source), and/or left unused within the device (which also contributes to waste and potential contamination).

Some devices are configured to limit the amount of medicament channeled or nebulized during patient expiration. For example, some devices rely on electronic timers or mechanical baffles to try to align nebulization and delivery of medicament to a patient's inspiration/expiration cycle so as to only nebulize and deliver medicament during patient inspiration. However, the use of such devices still results in waste of the medicament. When inspiration ends, a residual amount of medicament that has already been nebulized and/or channeled toward the patient, but that has not yet been received by the patient, is left unused within the device or is undesirably passed out of the device upon subsequent patient expiration. Moreover, existing devices are unable to adjust to differences in breathing patterns between different patients and/or variable breathing patterns of a particular patient (since every breath of a patient is not the same as every other breath by that patient but can change depending on the patient's state of consciousness, emotional state, or choice of activity). Breathing patterns may vary according to 1) frequency of inspirations, 2) duration of each individual inspiratory cycle, 3) proportion of time during inspiration and expiration, and 4) force of breath during each unique inspiration, for example.

Nebulized medicament left unused within the device can also undesirably recoalesce within the device before subsequent patient inspiration, rendering the medicament undeliverable to the patient. For example, a significant amount of nebulized medicament remaining in the device at the end of patient inspiration can recoalesce from a fine mist into larger droplets or a liquid film, a form not conducive to being delivered to a target nasopharyngeal area as intended. Undesirable coalescence can occur upstream and/or downstream of the patient breathing unit.

Further, typical devices do not operate under a positive pressure, or only operate under positive pressure in conjunction with patient inspiration. Thus, there can be a residual amount of medicament remaining in the device at a terminal phase of inspiration and/or at the end of inspiration that is not subjected to necessary positive pressure to deliver the residual medicament to the patient.

In addition, techniques that rely on preset timers that assume a hypothetical duration of inspiration and/or that rely on other lagging indicators (such as a previously measured breath cycle) cannot account for changes in a patient's breathing pattern from breath to breath. A significant portion of a patient's breathing can therefore be out of sync with the pre-determined medicament and/or gas delivery, resulting in wasted medicament and less efficient patient treatment.

The wasted amounts of medicament resulting from use of such devices and methods can be particularly costly when expensive medicaments, such as stem cells, platelets, or other biologics are required as part of patient treatment. There has been and continues to be a need for devices and methods for efficient nasopharyngeal and pulmonary delivery of medicament with reduced waste of medicament.

BRIEF SUMMARY

The present disclosure is directed toward devices and methods for delivering medicament to the nasopharyngeal and/or pulmonary areas of a patient with eliminated or reduced waste of medicament.

One or more embodiments of the present disclosure relate to a respiratory system that includes a nebulizer containing a medicament. The nebulizer may be, for example, powered by a pressurized gas source or electrically activated. The nebulizer can also be coupled to a breathing unit, such as a breathing mask, breathing tube, or a nasal pillow. A pressure sensitive mechanism (e.g., pressure sensitive switch or air flow detector) can detect negative pressure at the breathing unit caused by a patient's inspiration and can control nebulization of the nebulizer. For example, the pressure sensitive mechanism can open to provide flow of the pressurized gas to the nebulizer, or can activate an electric circuit to cause nebulization of the material.

The pressure sensitive mechanism can be configured to cease nebulization prior to the end of the patient's inspiration, upon reaching a threshold pressure or airflow, thereby allowing residual medicament disposed within the system to be cleared out of the system and inhaled by the patient during the remainder of the inspiration cycle. A compressor can also be included to provide positive pressure and to aid in the delivery of the medicament to the patient. The device can be configured to dynamically adjust to changes in breathing patterns by the patient and/or among different patients as discussed below.

Embodiments of the present disclosure can improve the efficacy of treatments of degenerative processes. Certain embodiments can improve the efficiency by which medicaments, such as stem cells, platelets, growth factors, vesicles, nucleic acids, and/or cytokines are introduced into a person or animal. By administering these substances under positive pressure with materials which increase the permeability of cell membranes and activating a nebulizer in synchrony with the appropriate portions of inspiration, these substances can be more efficiently introduced to the patient.

Administering medicaments through the nasal cavity can also allow the introduction of medications, stem cells, growth factors, vesicles, nucleic acids, and/or other trophic factors into the olfactory bulb. This can therefore provide access to the central nervous system and other organs outside the blood brain barrier through reverse axonal transport, perilymphatic channels, vascular, or as yet undefined mechanisms. In addition, administration of medicaments to the pulmonary system and associated circulatory systems can provide access to the respiratory system and associated pulmonary and systemic vascular system through direct absorption.

Moreover, patients with and without respiratory disease have varying degrees of difficulty sustaining normal inspiratory pressures for prolonged periods of time and may become short of breath and thus unable to inhale all medication during a treatment. With positive airway pressure, it is easier for patients to inspire, and therefore better patient compliance is likely to be achieved. Such positive pressure can be particularly used at a later portion of the respiratory cycle to assist the patient in the inspiration of air and delivery of medicament.

In some embodiments, the nebulizer can be activated at repeating intervals so that the medicament is nebulized at the beginning of the inspiratory cycle and then nebulization is stopped before the end of the inspiration phase of the respiratory cycle. This allows the remainder of the inspiratory breath to clear the chamber of nebulized material, which leaves minimal, if any, medicaments in the chamber unused. During expiration, the expiratory breath can be exhausted via a HEPA (high efficiency particulate arrestance) filter (e.g., which can protect the device from backflow contamination and/or prevent medicament from being expelled into the room outside the respiratory system.

One or more embodiments of the present disclosure may be used to treat symptoms of cystic fibrosis and/or other pulmonary conditions. In addition, one or more embodiments of the present disclosure are capable of providing precise quantities of medicament to be injected. This can be particularly beneficial, for example, with the use of stem cells, extracellular vesicles, macroproteins, nucleic acids, and other biologics or pharmaceuticals, which can cause an inflammatory reaction at doses which are too high. In addition, delivery of medicaments to the CNS (e.g., through the cribriform plate via tracts and passages associated with the olfactory nerves and bulbs into the intracranial space). In some embodiments, administration under positive pressure (e.g., higher than ambient) can allow greater penetration of medicament to and into the alveoli, past the cribriform plate, or other targeted anatomy.

These and other advantages and features of the embodiments disclosed herein will become more fully apparent from the following description and appended claims.

BRIEF DESCRIPTION OF THE DRAWINGS

To further clarify the above and other advantages and features of the present invention, a more particular description of the invention will be rendered by reference to specific embodiments thereof which are illustrated in the appended drawings. It is appreciated that these drawings depict only an illustrative embodiment of the invention and are therefore not to be considered limiting of its scope. The invention will be described and explained with additional specificity and detail through the use of the accompanying drawings in which.

DETAILED DESCRIPTION

I. Introduction

Figure 1:
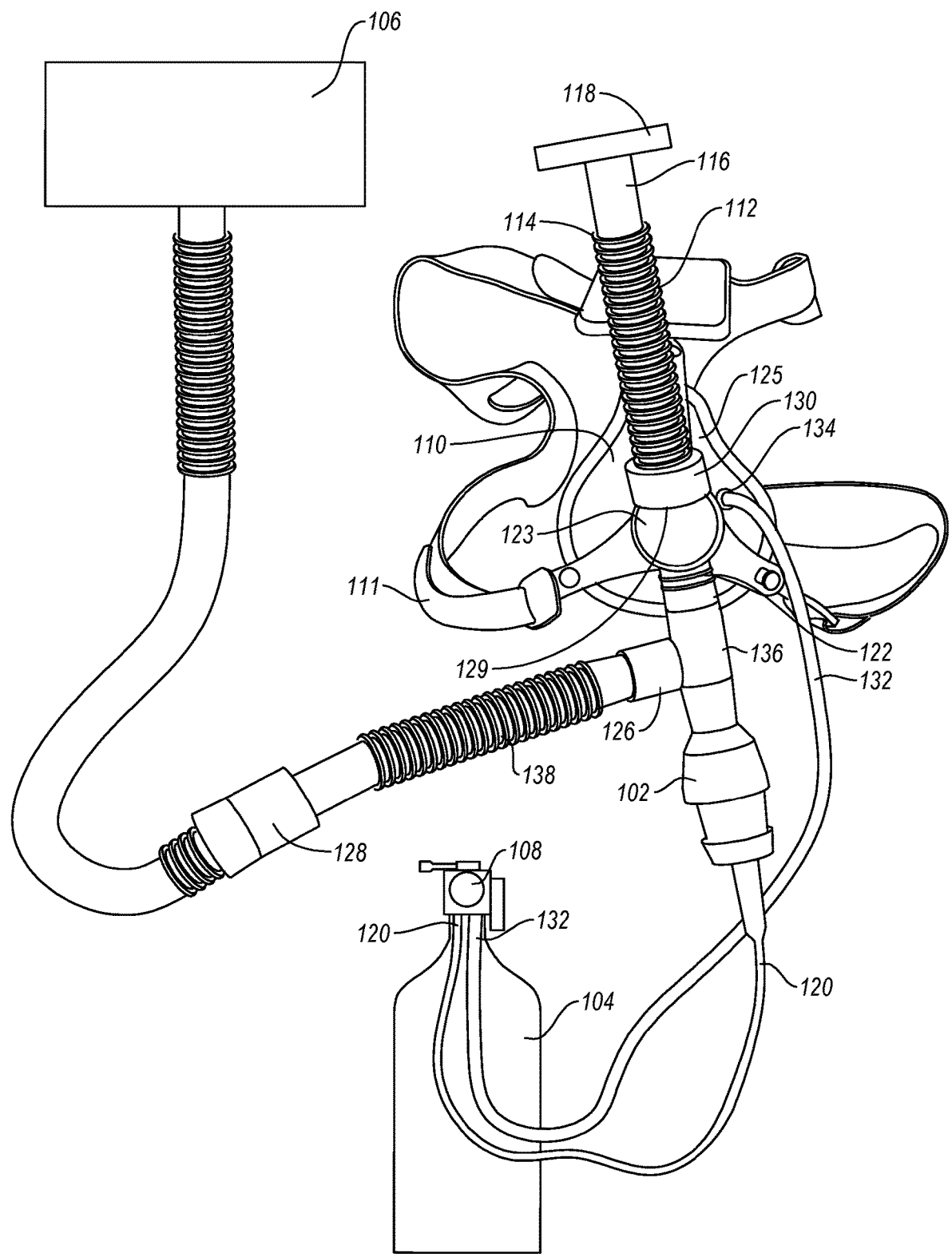
FIG. 1 illustrates an embodiment of a respiratory system as disclosed in this application.

One objective of the presently disclosed respiratory system is to deliver medicaments under positive pressure and at metered doses so as to prevent waste of the medicament. The medicament delivered by a nebulizer may include any medicament capable of being nebulized, including but not limited to, platelet rich plasma, stem cells, growth factors, cytokines, hyaluronidase, and other biologic and pharmaceutical medications. Target organs and/or organ systems can include the CNS (by way of the cribriform plate), pulmonary system, and circulatory system including vascular and lymphatic and extracellular circulatory systems. The system may be used to both treat a disease state as well as to rejuvenate and improve functioning of the pulmonary system, olfactory system, and associated tissues connected by the circulatory system, as well as the olfactory system and associated routes of entry into the central nervous system.

Treatment duration may vary from a few minutes to over an hour at a time. Treatments may initially be repeated on a daily basis or less frequently, and may be repeated at intervals during the year, depending on the underlying process being treated and degree of response of the patient.

Outcomes are measured based on physiological testing, such as pulmonary function test, physical endurance, as well as a subjective sense of improved endurance. When treating the central nervous system, imaging studies may be used to monitor progress and cognitive functioning testing may be performed.

The apparatus may also be used for administering pharmaceutical medications, synthetic materials, and chemotherapy medications. Essentially any solution or suspension may be introduced with the apparatus.

II. Exemplary Medicaments

Primary healing and regeneration can be achieved by the introduction of stem cells, proteins, vesicles, platelets which are either intact or lysed. They may be introduced with associated growth factors and cytokines. The described embodiments, in contrast to currently available techniques, can decrease waste of nebulized material, improve absorption, ease the patient's workload, improve patient ability to cooperate with treatments, and therefore may improve efficacy of treatment and patient compliance with treatment.

Increased cell permeability and increased penetration of medicaments can be achieved with medications such as hyaluronidase. In particular, hyaluronidase may be utilized to loosen barriers and allow delivered stem cells or other medicaments to better reach the nerves and circulatory pathways of the olfactory plate.

Preferred embodiments can include administering the medicaments under positive airway pressure, which can increase the transmural pressure and therefore absorption of the medicaments. The effectiveness of hyaluronidase can be increased by administering at neutral pH levels, which may be achieved by using a phosphate buffer saline or other buffered solutions. Such pH neutral hyaluronidase can then be used to pretreat the biological absorptive surface prior to delivering stem cells and/or other factors. Alternatively, stem cells and/or other factors may be suspended in hyaluronidase and then delivered. Various concentrations may be used. For example, suspending cells in about 5 to 45 micrograms, or about 10 to 40 micrograms, or about 15 to 30 micrograms, or about 20 to 25 micrograms of a solution including hyaluronidase at a concentration ranging from about 1 to 20 mg/ml, or about 5 to 15 mg/ml, or about 10 mg/ml. In some embodiments, about 20 micrograms of a stem cell medicament (which may include cytokines and/or other factors) is suspended in a solution including hyaluronidase at a concentration of about 10 mg/ml.

Platelet rich plasma and growth factors can be obtained from blood plasma. Stem cells may be obtained from mesenchymal stem cells in adipose tissue, from bone marrow aspirate, blood, and/or from other sources. The samples may be obtained following standard protocols for obtaining such samples. After collection, cells may be administered immediately after purification and concentration, or after further cell line expansion to increase cell load to be injected.

For example, in the case of platelet rich plasma and growth factors, blood samples may be taken and centrifuged, with the desired components aspirated from the centrifuged samples. The aspirated components can then be pooled and placed into the nebulizer.

Stem cells can be obtained from adipose tissue, blood, and/or bone marrow with standard harvesting techniques, followed by washing and resuspension. Viability of the harvested material is ensured by the use of fresh material which is reintroduced into the body within two hours of harvesting. Other methods of preserving the harvested material include refrigeration, freezing, and incubation to produce cell line expansion. Freezing of cells can result in the production of lysate which may further improve efficacy of treatment.

The particle size of stem cells or other medicament can be selected to provide targeted treatment to a particular region or regions of lung tissue, such as selecting different particle sizes when targeting one or more of the alveoli, bronchi, and/or nasopharynx.

The vehicle for delivery of the medicament varies depending on the type of medicament that is used for the treatment and the delivery target. It may be necessary or desirable to suspend or mix the treatment material in a carrier or other pharmaceutically acceptable substance. For platelet rich plasma, the plasma itself can act as a carrier but may be supplemented with other materials so as to change viscosity and/or increase cell penetration. Stem cells may be suspended in saline. Cell suspension and efficacy may be improved with the use of pH neutral solutions and optimized hyaluronidase concentrations.

Delivery of stem cells and/or other biologics via the respiratory system can beneficially reduce risk as compared to other conventional delivery routes. For example, there is risk associated with intravenous delivery of stem cells because of the possibility that the stem cells will clump together and cause ischemic stroke or other problems.

III. Delivery Devices

FIG. 1 illustrates an exemplary embodiment of a respiratory system. FIG. 1 shows a nebulizer 102 which can be propelled by tank 104 containing compressed oxygen or air. Other embodiments may additionally or alternatively utilize an electronically actuated nebulizer. Airflow pressure from the nebulizer 102 can be increased to the breathing unit worn by the patient by a compressor 106 (such as a Biphasic Positive Airway Pressure (BiPAP®)) or other positive pressure components, which can have variable pressure and can be modulated. In preferred embodiments, the compressor 106 is biphasic so that higher positive pressures are delivered during patient inspiration than during patient exhalation. This beneficially assists the patient during inspiration, enabling the patient to take deeper breaths and allowing the medicament to be better delivered to the target (e.g., alveoli), while also ensuring that the same positive pressure is reduced during patient exhalation so as to allow good exhalation from the patient without the patient having to fight against excessive positive pressure.

The compressor 106 feeds compressed air to the breathing unit downstream from the nebulizer 102 via air line 138 to facilitate more complete patient breathing and more complete delivery of nebulized medicament to the patient, as depicted in FIGS. 1 and 3 and discussed more fully below. Flow from tank 104 may be controlled by a negative pressure sensitive switch 108, activated by negative pressure generated in a breathing unit, illustrated in this embodiment as breathing mask 110. Other embodiments may include a different pressure sensitive mechanism, such as a pressure transducer or air flow detector.

The nebulizer 102 is preferably a jet nebulizer configured to provide a fine mist of nebulized medicament in response to the passage of compressed air through the nebulizer 102. Such jet nebulizers can beneficially allow the use of medicaments including larger proteins, cells, and cell components. In other embodiments, the nebulizer 102 may be formed as an ultrasonic nebulizer or other form of nebulizer. The nebulizer 102 may be positioned upstream or downstream of the positive air pressure support delivered by the compressor 106.

As used herein, the terms "nebulize," "nebulizer," "nebulized," and the like relate to the production of mist to be delivered to the nasopharyngeal and/or pulmonary tissues of a patient. As used herein, such terms are synonymous with "aerosol," "aerosolizer," "aerosolized," "inhaler," "inhalant," and the like.

An exhaust manifold 112 may be connected to the mask 110 and can contain at its distal end 114 a one-way valve 116 and filter 118 (e.g., a high-efficiency particulate arrestance ("HEPA") filter). The one-way valve 116 and HEPA filter can prevent backflow of contamination into exhaust manifold and also prevent medicament from being expelled into the room. Breathing mask 110 as shown can be designed to fit over a patient's nose and/or mouth and can have straps 111 or other attachment means to help fix the mask 110 in position on a patient. In other embodiments, breathing mask 110 may alternatively be configured as a nasal pillow mask, a nasal mask, a mouth-only mask or tube, or other type of delivery structure configured to enable delivery of air and/or medicament to a patient's nasopharyngeal and/or pulmonary systems.

Figure 2:
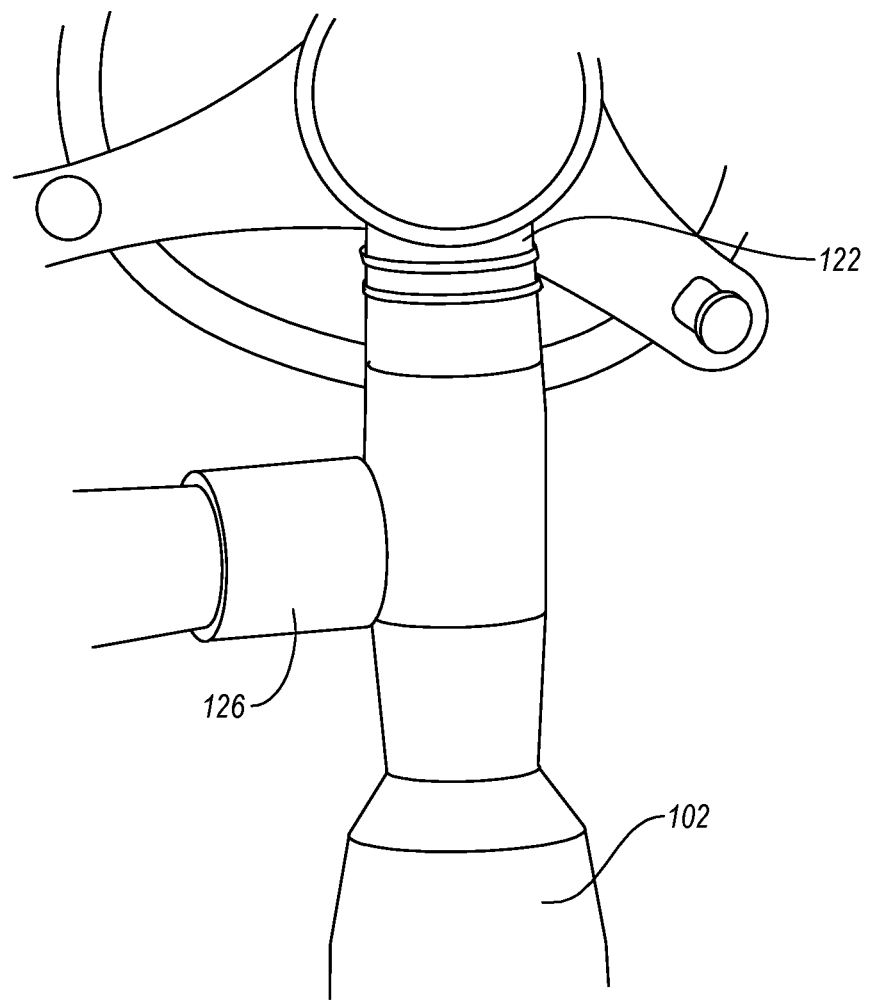
FIG. 2 illustrates a close-up view of a nebulizer of the respiratory system of FIG. 1, and associated components.
Figure 3:
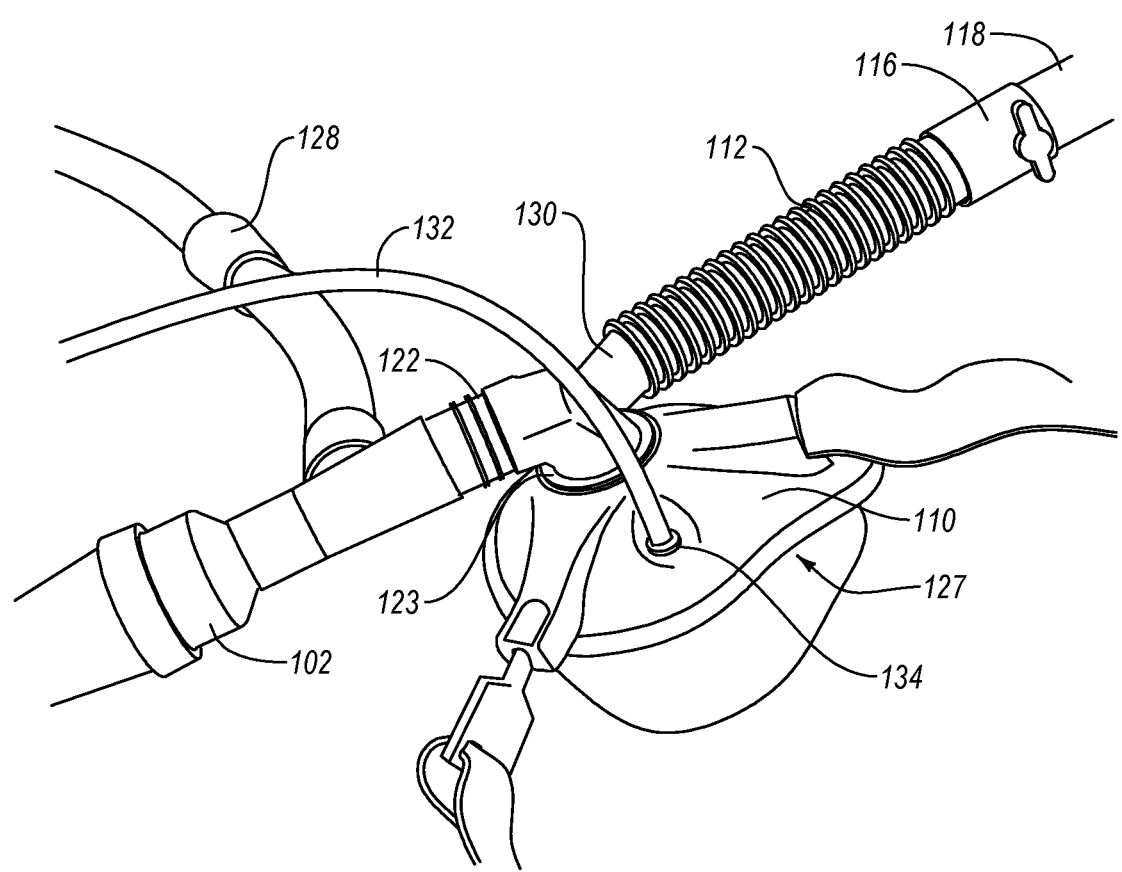
FIG. 3 illustrates a side view of the respiratory system of FIG. 1.

Oxygen, air, or other gas can flow from tank 104 to nebulizer 102 through a gas line 120. Airflow direction and rate can be controlled by negative pressure generated as well as positive pressure generated by the compressor 106. Several valves (e.g., one-way valves) throughout the system can ensure proper airflow. Valve 122, which can be configured as a lower pressure valve (e.g., is actuated at lower pressures relative to other valves of the device), can be located in the mask 110 or mask assembly. As depicted in FIGS. 1-3, a connection conduit 136 feeding valve 122 can serve to place the compressor 106 and nebulizer 102 in closed fluid communication with the breathing mask 110. Medicaments and/or gas can flow from the nebulizer 102 and compressor 106 through valve 122 and into the breathing mask 110. Valve 122 can be configured to close prior to the opening of valve 116 (e.g., by configuring valve 122 to actuate at a lower pressure threshold relative to valve 116), thereby ensuring that the patient's expiratory volume exits through the exhaust manifold 112 rather than air and nebulized medicament being permitted to flow back toward the nebulizer 102 and the compressor 106, which might interfere with proper functioning of the nebulizer 102 and/or deposit medicament on surfaces within connection conduit 136 and/or air line 138.

FIG. 2 is a close-up view of the nebulizer 102 and nearby components of the system 100 illustrated in FIG. 1, including the connection conduit 136, which combines pressurized gas streams from the nebulizer 102 and compressor 106 and delivers them through the valve 122 and into the breathing unit. The nebulizer 102 in this embodiment can be powered by compressed oxygen and/or compressed air (e.g., delivered through tank 104, pressurized gas line, or other compressed gas delivery means). Pressurized air from the compressor 106 passes through connection conduit 136 and assists in moving nebulized material from the nebulizer 102 to the breathing mask 110.

Referring back to FIG. 1, the nebulizer 102 can be activated by a negative pressure sensitive switch 108, which may be disposed on tank 104 as illustrated or at other sections of the device providing access to the gas line 120. Face mask 110 can be connected to a trigger hose 132 (e.g., via mask trigger port 134), which is also in communication with the pressure sensitive switch 108. When a patient wearing mask 110 inspires, the pressure in the trigger hose 132 can drop and can trigger the pressure sensitive switch 108. In the illustrated embodiment, when the switch 108 is activated by negative pressure during patient inspiration, airflow is provided to the nebulizer 102. As will be appreciated by one having skill in to art, placing the trigger hose 132 in direct communication with the patient's breathing via mask trigger port 134, downstream from connection conduit 136 and valve 122, ensures accurate opening and closing of switch 108 in response to the patient's breathing, including being able to accurately respond to changes in patient breathing patterns.

As mentioned above, other embodiments may utilize alternative arrangements of respiratory system components. For example, a pressure transducer and/or nebulizer may be positioned within the patient mouthpiece rather than on or within components disposed exterior to the patient mouth. The mouthpiece can be directed toward the patient's pharynx during use by the patient. The pressure transducer can turn pressurized air flow on and off via an electric signal.

Medicament, such as stem cells, platelet rich plasma, other medicaments described herein, or other medicaments useful for nasopharyngeal and/or pulmonary delivery, can be located in the nebulizer 102. Such medicament may be positioned in the nebulizer 102 before the system 100 is assembled or may be injected or otherwise positioned into the nebulizer after assembly is partially or totally completed.

The medicament in the nebulizer 102 can be aerosolized by the gas from the tank 104, and the nebulized particles can travel through the device toward and then through the connection conduit 136 and valve 122 to be inhaled by a patient wearing mask 110. The valve 122 may connect to a mask inlet port 123 that allows the passage of gas and medicament between an outer surface 125 of the face mask and an inner surface 127 of the face mask.

The nebulizer 102 may also be triggered manually to adjust the timing of the delivery of nebulized medicament during the initial portion of the inspiratory phase. For example, the system 100 can include a manual trigger actuator configured such that a patient or caretaker can manually actuate (via button, knob, switch, etc., not shown) the pressure sensitive switch 108 in order to initiate compressed air flow from tank 104 and nebulization of the medicament within the nebulizer 102.

In preferred embodiments, after actuation, the manual trigger actuator is configured to maintain automatic closing of pressure sensitive switch 108 when the amount of negative pressure lessens to below a threshold level. As explained in more detail below, such functionality can beneficially allow residual medicament remaining in the device to be cleared from the device and delivered to the patient during the terminal phase of the inspiration phase. More complete delivery of medicament to the patient is enhanced by interconnecting the nebulizer 102 with compressor 106 via the connection conduit 136 and providing valve 122, which as depicted and arranged, prevents the backflow of exhaled air and medicament toward the connection conduit 136, nebulizer 102, and compressor 106. Other arrangements of connection conduit 136 and/or valve 122 are also envisioned.

In some embodiments, a controllable valve 108, such as a solenoid valve (e.g., in conjunction with a programmable controller/regulator) may be used to stop the flow of nebulized material prior to the end of inspiration, thus allowing for inspiration of all material in the inspiration mask, thereby reducing waste of medicament. For example, the controller can cause the valve 108 to stop the flow of gas according to a preset time. In preferred embodiments, however, gas flow and nebulization of medicament is stopped based on real-time determination of inspiration parameters, as described in more detail below.

FIG. 3 illustrates another view of the system 100 showing the placement of the valves 128, 126, 122, 116, and 130. Valve 122 can be positioned so as to prevent the backflow (toward the connection conduit 136, nebulizer 102, and compressor 106) of expired breath during expiration. The closure of the valve 122 during expiration thus forces air to travel into the exhaust manifold 112 and out through the one-way valve 116. Valve 130 can be positioned so as to prevent passage of medicament-containing air into the exhaust manifold 112 during inspiration, thereby minimizing waste of the medicament and/or depositing of medicament onto the walls of the exhaust manifold 112. Valve 130 may be controlled by manual switching and/or may be automatically actuated according to appropriate pressure changes (e.g., closes at lower pressures during inspiration and opens at higher pressures during expiration). In some embodiments, the valve 130 may connect to an outlet port 129 (see FIG. 1) that allows the passage of gas and/or medicament between an outer surface 125 of the face mask 110 and an inner surface 127 of the face mask 110 (e.g., for a small portion of gas and/or medicament not first passing through inlet port 123, thereby minimizing waste of such gas and/or medicament). Valves 126 and 128 can control and/or channel gas flow from the compressor 106 (not shown in FIG. 2). For example, valves 126 and/or 128 can prevent backflow (flow toward the compressor 106) of air or gas and nebulized medicament from the nebulizer 102 directed toward the patient.

Referring to FIG. 1, the connection conduit 136 between the nebulizer 102 and the inlet port 123 may be T-shaped or Y-shaped. The connection conduit 136 may connect to the valve 126, which may connect to the air line 138, which may connect to the compressor 106 (e.g., a Biphasic Positive Airway Pressure (BiPAP®) compressor).

IV. Efficient Delivery of Medicament

One or more embodiments of the present disclosure can improve the efficiency by which stem cells, platelets, growth factors, cytokines, vesicles, nucleic acids, and/or other medications are introduced into a person or animal. For example, by administering these medicaments under positive pressure (e.g., as a result of the compressor 106), and activating a nebulizer 102 (such as by opening the valve 108 of tank 104 or electrically activating the nebulizer 102) during the appropriate portions of the inspiratory cycle, these medicaments can be more efficiently introduced.

Moreover, patients with and without respiratory disease have varying degrees of difficulty sustaining inspiration against resistance for prolonged periods of time and may become short of breath. With positive airway pressure, it is easier for patients to inspire, and therefore better patient compliance is likely to be achieved.

In some embodiments, nebulizer 102 can be actuated intermittently so that the medicament is nebulized at the beginning of the inspiration phase of a respiratory cycle and then nebulization is stopped before the end of the inspiration phase of the respiratory cycle. This allows the residual amount of medicament to be cleared from the device as it is delivered to the patient during a terminal phase of inspiration (e.g., the portion of inspiration following cessation of nebulization). Such a configuration can leave minimal, if any, unused medicament in the lines, tubing, valves, mask 110 (e.g., the space between the inside surface of mask 110 and the patient's face), and other portions of the device. Substantially clearing the medicament is beneficial because it avoids the tendency of medicament to coalesce into larger droplets on the inner surfaces of the lines, tubing, valves, mask, etcetera. In other words, simply waiting for the patient to inhale again can still involve loss of medicament because much of it may have already coalesced into larger droplets which are then less likely to be effectively delivered to the intended target, particularly when the intended target is alveoli deep within the patient's lungs.

In some embodiments, the pressure sensitive switch 108 can be a pressure regulated switch (e.g., electrical, mechanical, or electromechanical) configured to allow adjustment of one or more pressures at which the switch will open and/or close. For example, the pressure sensitive switch 108 (or other pressure sensitive mechanism) can be communicatively coupled to a control circuit (i.e., controller) that is programmable to provide selection and adjustment of a nebulization actuation pressure and/or a cessation pressure. The pressure sensitive switch 108 may be configured as a pressure transducer.

Preferably, the controller is configured to dynamically adjust the nebulization actuation pressure and/or cessation pressure based on measurements of variable patient breathing. This allows the system to adjust to particular patient breathing conditions and to tune nebulization to the patient's dynamically changing inspiration patterns. In some embodiments, the controller operates to adjust nebulization actuation pressure and/or cessation pressure in real-time. As used herein, "real-time" refers to measurements taken during the same respiratory cycle (i.e., the same patient breath) in which potential adjustments to the system are made. For example, the controller may be configured to take "real-time" pressure measurements during a patient breath and adjust one or more threshold pressures during the same breath. In other embodiments, the controller may utilize previous breaths (such as a rolling average of the previous 3, 5, 10, 15, 20, 30 breaths, etc.) to set the nebulization actuation and/or cessation pressures, while continually updating the nebulization actuation and/or cessation pressure as the patient takes additional breaths.

As mentioned above, breathing cycles will vary from patient to patient and will also vary within the same patient from breath to breath. Thus, simply trying to align nebulization with part or all of the inspiration phase via a set timer or a set of static, non-adjustable pressure thresholds are overly crude approaches that lack the flexibility and versatility needed to effectively align medicament delivery with the intended (e.g., beginning) portion of the inspiratory phase.

The controller may include, for example, one or more processors and memory (e.g., one or more hardware storage devices). The memory may include executable instructions that are executable by the one or more processors of the controller to carry out the controller functionality described herein.

Figure 4:
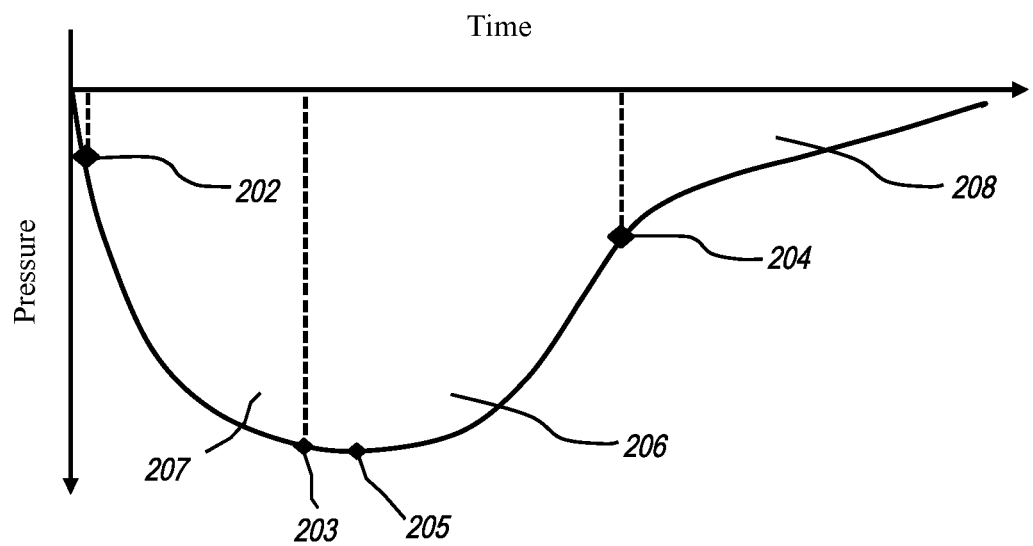
FIG. 4 illustrates the change in alveolar pressure over time during an inspiration phase of a typical respiratory cycle, showing a terminal phase of inspiration, in which residual medicament may be cleared from the respiratory system and delivered to a patient.

FIG. 4 schematically illustrates alveolar pressure change over time during a typical inspiration portion of a respiratory cycle, with the curve showing the change in negative pressure as a function of time for an illustrated inspiration portion of the respiratory cycle. As illustrated, the curve shows decreasing alveolar pressure during a first inspiration phase, as depicted by a negative slope.

As the patient continues to inhale, the magnitude of the negative slope decreases, with peak negative pressure occurring where the slope becomes zero at the end of the first inspiration phase (defining a local minimum of the pressure curve).

At the beginning of the second inspiration phase, the slope of the curve turns positive, indicating increasing alveolar pressure (back toward ambient). During the second inspiration phase, the slope of the pressure curve increases as the curve progresses along the time axis. An inflection point in the curve marks the end of the second inspiration phase and beginning of the third inspiration phase. During the third phase, the magnitude of the slope begins to decrease (i.e., becomes less positive but still overall positive), which corresponds to slower deceleration of inhalation as the patient progresses toward the end of the inspiration portion of the respiratory cycle.

One having skill in the art will appreciate that the transitions between first, second, and third inspiration phases can occur at different particular times along the timeline, depending on the patient's breathing pattern. In some embodiments, the first and second inspiration phases can correspond to an "initial inspiratory phase" and the third inspiration phase can correspond to a "terminal inspiratory phase".

In mathematical terms, the transition from first inspiratory phase to second inspiratory phase represents a root of the first derivative of the pressure curve (where the first derivative changes from negative to positive), whereas the transition from second inspiratory phase to third inspiratory phase represents a root of the second derivative of the pressure curve (where the second derivative changes from negative to positive).

As further illustrated in FIG. 4, a pressure sensitive mechanism (e.g., a pressure transducer or pressure switch 108 as in FIGS. 1-3) can be configured to actuate (so as to provide nebulization and delivery of medicament) upon sensing a first threshold pressure at point 202, which is located at or near the beginning of the first inspiration phase of the respiratory cycle. The pressure sensitive mechanism can also be configured to cease delivery of medicament upon reaching a second threshold pressure. The second threshold pressure may be located at point 203, point 204, or at a location on the pressure curve between points 203 and 204.

Point 203 is located just prior to the point of maximum inhalation pressure (minimum alveolar pressure), represented by point 205, marking the end of the first inspiration phase and beginning of the second inspiration phase. Point 204 is located at or near the inflection point of the curve at the end of the second inspiration phase and beginning of the third inspiration phase.

For an embodiment where nebulization continues to point 204, the time periods 207 and 206 indicate the time during which medicament is being nebulized and delivered to the patient, which is illustrated as occurring during the first and second inspiration phases. Time period 208 indicates the terminal phase of the inspiration phase, which is illustrated as occurring during the third inspiration phase. In this time period, residual medicament residing within the device (e.g., within the tubing, lines, valves, mask, and/or space between the mask and face) can be partially or fully cleared from the device and delivered to the patient as intended (e.g., during the third inspiration phase as illustrated). In addition, in some embodiments, continued positive pressure (e.g., from a compressor such as a BiPAP® compressor) further directs residual medicament and gas volume into the nasopharyngeal and/or pulmonary areas of the patient to deliver the medicament and prevent wasted medicament.

In other embodiments, threshold pressures at points 202, 203, and/or 204 can be adjusted according to patient and/or care provider needs and preferences. For example, first threshold pressure 202 can be adjusted to provide reliable initiation of nebulization and gas flow. Additionally, or alternatively, the second threshold pressure (at 203, 204, or therebetween) can be adjusted to provide an adequate balance between time period 207 in which nebulization is active and time period 208 in which medicament is cleared. Time period 206 may correspond to active or inactive nebulization, or may be split between the two, depending on where the cessation threshold is located between points 203 and 204.

In addition, setting the second threshold pressure (cessation threshold pressure) to be at or near the local minimum (such as at point 203), at or near the inflection point (such as at point 204), or some point therebetween, permits adjustment of the timing of nebulization in order to account for both inter- and intra-patient variability in breathing patterns. FIG. 4 illustrates that the second threshold pressure may be located at a point in time where there is both an absolute pressure reading and a measurable/detectable pressure curve feature (e.g., a local minimum separating the first and second inspiration phases or an inflection point separating the second and third inspiration phases), for any given breathing cycle. This permits the system to more accurately detect and self-adjust to changes in breathing pattern across patients and to changes in breathing pattern within the same patient. This, in turn, provides an important technical advantage over systems that can only set the timing of nebulization timing according to some preset, static threshold and/or according to a timer.

As an example of how the system can determine that the second threshold pressure has been reached, the controller may sample the pressure at a rate sufficient to allow an estimation of the present slope of the pressure curve. As explained above, the slope will initially be negative, but will begin to approach zero as the curve advances to the point of minimum pressure at point 205. The controller can determine that the point 203 has been reached once the slope is nearly zero but is still negative. For example, the controller may determine that point 203 has been reached if the rate of slope change suggests that the slope will reach or pass zero within the next few sampling reads. In some implementations, the controller can determine that point 203 has been reached when the slope of the pressure curve is measured as greater than about −0.125 mm Hg per second, or greater than about −0.1 mm Hg per second, or greater than about −0.05 mm Hg per second, or greater than about −0.025 mm Hg per second.

The controller may be configured to determine point 205 as the point where the slope reaches zero and begins to turn positive. The inflection point at 204 may be determined as the point where the slope is positive but begins to decrease over time.

As explained above, the second threshold pressure may be set to correspond to point 203, point 204, or a point on the pressure curve therebetween. During use of the system, the controller can operate to initiate nebulization early during inspiration, such as at point 202. Point 202 may correspond to a pressure, for example, of about −0.05 mm Hg to about −0.5 mm Hg, or more typically about −0.1 mm Hg to about −0.25 mm Hg. As the patient continues to inhale, the controller operates to detect one or both of points 203 and 204 and operates to cease nebulization at some pressure located at or between points 203 and 204.

The controller may determine one or more of points 202, 203, 204, or 205 in real-time during a patient breath and adjust one or more threshold pressures during the same breath. Alternatively, the controller may utilize previous breaths (such as a rolling average of the previous 3, 5, 10, 15, 20, 30 breaths, or some other suitable number) to set the nebulization actuation and/or cessation pressures, while continually updating the nebulization actuation and/or cessation pressure as the patient takes additional breaths and additional inspiration curve data is gathered.

In addition, during expiration, the expiratory breath can be exhausted via filter 118 (e.g., HEPA filter). Filter 118 can be configured to prevent uninspired stem cells or other materials (if any) from exiting the system. Filter 118, in coordination with valve 130, can also prevent contamination from entering the exhaust manifold 112.

Embodiments of the present disclosure can provide a number of benefits. For example, the system can be configured to prevent nebulization during expiration, during resting periods between breaths, and during a terminal phase (e.g., third phase) of inspiration, as illustrated in FIG. 4. In addition, the system does not rely on static pressure thresholds and/or preconfigured timing sequences attempting to match nebulization and the breathing cycle to a consistent pattern. For example, the device can operate to efficiently deliver nebulized medicament and preventing waste even if the patient has an inconsistent or erratic breathing pattern, such as a short, shallow breath followed by a deep, long breath, or vice versa. Further, the device does not rely on lagging indicators (such as one or more of the previous breath cycles) to estimate current breath activity, but instead operates in real-time to deliver medicament during inspiration without over-providing and wasting medicament.

Moreover, the actuation and cessation of nebulization does not require monitoring of the compressor or the determination of compressor-related parameters. For example, the pressure sensitive mechanism can turn nebulization on and off according to criteria that are independent of operation of the compressor.

Figure 5:
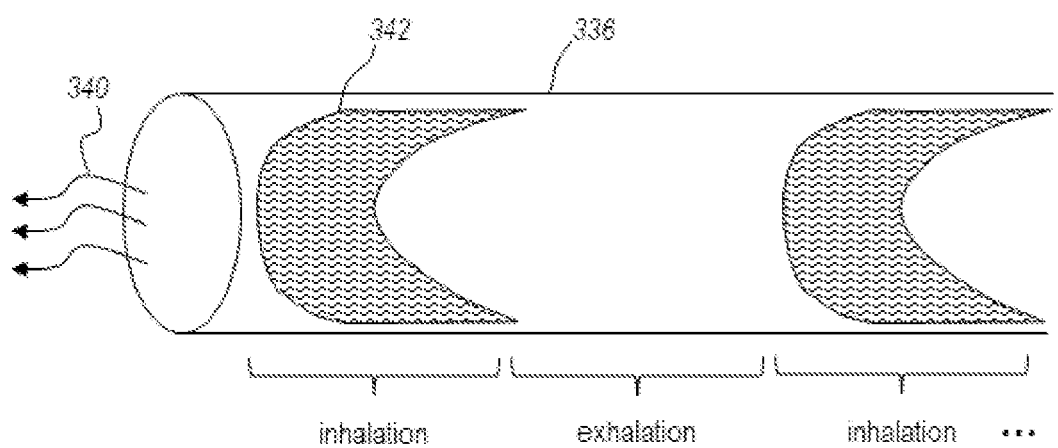
FIG. 5 is a schematic conceptually illustrating the timing of medicament delivery with respect to patient inspiration and exhalation.

FIG. 5 is a schematic that conceptually illustrates some of the principles discussed above as they relate to timing of medicament delivery. FIG. 5 shows a simplified representation of a conduit 336. Arrow 340 indicates the direction of airflow through the conduit, and represents airflow from the nebulizer toward the breathing unit. As shown, medicament is delivered through the conduit 336 in a series of boluses 342. Each bolus 342 is associated with an initial portion of a patient inspiration cycle, whereas the conduit is free of medicament at portions corresponding to the terminal phase of inspiration and to exhalation.

V. Trans-Cribriform Plate CNS Administration

In some embodiments, the device can be directed toward the olfactory epithelium and bulb. This can be accomplished by adjusting the positive airway pressure to a variable frequency pulsing at about 2 to 200 Hz, or about 25 to 150 Hz, or about 50 to 100 Hz. In some embodiments, the face mask 110 can include a nasal adaptor configured to direct nebulized medicament to the cribriform plate of the patient. For example, the nasal adaptor can include sealed prongs to seal the nasal passageways and variable length extension tubes directed to the cribriform plate. In this configuration, positive pressure provided at variable pulse frequency and/or velocity can enhance flow to the cribriform plate of the patient.

In some embodiments, the nasal adaptor of the face mask 110 can include a first sealed prong for positioning in a first nostril of a patient, and a variable length extension extending from the first sealed prong toward the cribriform plate. The second nostril can be sealed with a second prong including a one way valve configured to allow outflow of gas and nebulized medicament introduced through the first nostril. Positive pressure may also be provided at variable velocity and/or pulse frequencies to enhance flow to the cribriform plate.

In some embodiments, the face mask 110 may also include an expiratory tube insertable into a patient's mouth. The expiratory tube may enable a patient to blow air through and breathe through the tube so as to conscientiously close the soft palate. Embodiments utilizing such an expiratory tube may be useful in circumstances where it is desired or required that nebulized medicament be passed to the olfactory bulb and not the pulmonary system. In addition, closure of the soft palate can be monitored by measuring the amount of pressure the patient exhales into the expiratory tube. For example, a pressure sensitive solenoid switch can be coupled to the gas flow, and can be configured to cut off gas flow to the nasal cavity upon sensing a pressure drop during patient expiration (e.g., drops below a threshold value during an otherwise normal expiration phase of a respiratory cycle).

The present invention may be embodied in other specific forms without departing from its spirit or essential characteristics. For example, the present invention may be modified for use with a ventilator and an endotracheal tube that is inserted through the mouth or nose (i.e., intubation), or through a breathing tube placed through the front of the neck via a tracheostomy. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

The invention claimed is:

1. A respiratory system for delivery of a medicament to a patient, the respiratory system comprising;
    a breathing unit;
    a nebulizer pneumatically coupled to the breathing unit and configured to nebulize a medicament and direct nebulized medicament into the breathing unit;
    a pressure sensitive mechanism configured to sense pressure within the breathing unit; and
    a controller communicatively coupled to the nebulizer and the pressure sensitive mechanism, the controller being configured to:
        initiate nebulization upon detection of a first threshold pressure corresponding to the beginning of patient inspiration, and
        to cease nebulization upon detection of a second threshold pressure, the second threshold pressure corresponding to a point prior to the end of patient inspiration to thereby cease nebulization of medicament while the patient continues to inspire through a terminal phase of inspiration,
    wherein the controller is configured to dynamically adjust the second threshold pressure according to measured variations in patient inspiration.

2. The respiratory system of claim 1, further comprising a compressor configured to provide positive air pressure to the breathing unit in order to assist delivery of the nebulized medicament to the breathing unit.

3. The respiratory system of claim 2, wherein the compressor is biphasic and configured to provide a first pressure during patient inspiration and a second pressure during patient exhalation, the first pressure being greater than the second.

4. The respiratory system of claim 2, further comprising a valve positioned between the breathing unit, the compressor, and the nebulizer and configured to prevent backflow of air or gas toward the compressor and the nebulizer.

5. The respiratory system of claim 2, further comprising a conduit connecting the nebulizer to the breathing unit, and an air line that extends from the compressor to the conduit to pneumatically connect the compressor to the conduit, the air line comprising one or more valves configured to prevent backflow of air or gas toward the compressor.

6. The respiratory system of claim 4, further comprising an exhaust manifold fluidly coupled to the breathing unit and configured to receive exhaled air from the patient upon closing of the valve.

7. The respiratory system of claim 6, further comprising at least one valve along the exhaust manifold configured to permit passage of exhaled air from the patient and to close during patient inspiration, and further comprising a filter coupled to the exhaust manifold to filter particles in the exhaled air.

8. The respiratory system of claim 1, wherein the nebulizer further includes a medicament, the medicament comprising one or more of stem cells, platelets, growth factors, cytokines, extracellular vesicles, proteins, and hyaluronidase.

9. The respiratory system of claim 1, wherein the nebulizer is a jet nebulizer or an ultrasonic nebulizer.

10. The respiratory system of claim 1, wherein the breathing unit is configured to deliver nebulized medicament to the cribriform plate of the patient.

11. The respiratory system of claim 1, wherein the controller is configured to dynamically adjust the second threshold pressure based on real-time pressure measurements of patient breathing.

12. The respiratory system of claim 1, wherein the controller is configured to determine slope of a pressure curve representing measured pressure over time, and to vary the second threshold pressure according to determined slope of the pressure curve.

13. The respiratory system of claim 12, wherein the controller is configured to:

define a first point as being after the first threshold pressure but before the slope of the pressure curve reaches zero, and to set the second threshold pressure to a pressure corresponding to the first point.

14. The respiratory system of claim 12, wherein the controller is configured to:

define a first point as being after the first threshold pressure but before the slope of the pressure curve reaches zero, define a second point as being at or near an inflection point where positive slope of the pressure curve begins to decrease, and to set the second threshold pressure to a pressure corresponding to the first point, second point, or point therebetween on the pressure curve.

15. The respiratory system of claim 12, wherein the controller is configured to:

define a second point as being at or near an inflection point where positive slope of the pressure curve begins to decrease, and to set the second threshold pressure to a pressure corresponding to the second point.

16. A respiratory system for delivery of a medicament to a patient, the respiratory system comprising;

a breathing unit;

a nebulizer pneumatically coupled to the breathing unit and configured to nebulize a medicament and direct nebulized medicament into the breathing unit;

a pressure sensitive mechanism configured to sense pressure within the breathing unit;

a controller communicatively coupled to the nebulizer and the pressure sensitive mechanism, the controller being configured to:

initiate nebulization upon detection of a first threshold pressure corresponding to the beginning of patient inspiration, and to cease nebulization upon detection of a second threshold pressure, the second threshold pressure corresponding to a point prior to the end of patient inspiration to thereby cease nebulization of medicament while the patient continues to inspire through a terminal phase of inspiration, wherein the controller is configured to dynamically adjust the second threshold pressure according to variations in patient inspiration and based on real-time pressure measurements of patient breathing; and a biphasic compressor configured to provide positive air pressure to the breathing unit in order to assist delivery of the nebulized medicament to the breathing unit, the biphasic compressor being configured to provide a first pressure during patient inspiration and a second pressure during patient exhalation, the first pressure being greater than the second.

17. The respiratory system of claim 16, wherein the controller is configured to determine slope of a pressure curve representing measured pressure over time, and to vary the second threshold pressure according to determined slope of the pressure curve.

18. The respiratory system of claim 17, wherein the controller is configured to:

define a first point as being after the first threshold pressure but before the slope of the pressure curve reaches zero, define a second point as being at or near an inflection point where positive slope of the pressure curve begins to decrease, and to set the second threshold pressure to a pressure corresponding to the first point, second point, or point therebetween on the pressure curve.

19. A method of delivering a nebulized medicament to a patient, the method comprising:

providing a respiratory system, the respiratory system comprising:

a breathing unit;

a nebulizer pneumatically coupled to the breathing unit and configured to nebulize a medicament and direct nebulized medicament into the breathing unit;

a pressure sensitive mechanism configured to sense pressure within the breathing unit;

and a controller communicatively coupled to the nebulizer and the pressure sensitive mechanism, the controller being configured to dynamically control initiation and cessation of nebulization according to variations in patient inspiration;

the nebulizer initiating nebulization upon the pressure sensitive mechanism detecting a first threshold pressure at the beginning of patient inspiration; and the nebulizer ceasing nebulization upon the pressure sensitive mechanism detecting a second threshold pressure, the second threshold pressure corresponding to a point prior to the end of patient inspiration to thereby cease nebulization of medicament while the patient continues to inspire through a terminal phase of inspiration; and adjusting the second threshold pressure according to pressure measurements from the pressure sensitive mechanism during a subsequent patient inspiration.

* * * * *